United States Patent [19]
Smith

[11] Patent Number: 5,572,994
[45] Date of Patent: Nov. 12, 1996

[54] OCCLUSION RESISTANT OXYGEN SUPPLY CONDUIT FOR A NASAL CANNULA

[76] Inventor: Steven W. Smith, 1077 NE. 35th St., Oakland Park, Fla. 33334

[21] Appl. No.: 479,941

[22] Filed: Jun. 7, 1995

[51] Int. Cl.⁶ .............................. A61M 15/08; A62B 9/04
[52] U.S. Cl. ................. 128/207.18; 128/DIG. 26
[58] Field of Search ......................... 128/207.18, DIG. 26

[56] References Cited

U.S. PATENT DOCUMENTS

| | | | |
|---|---|---|---|
| 4,875,718 | 10/1989 | Marken | 128/912 |
| 5,054,482 | 10/1991 | Bales | 128/207.14 |
| 5,222,486 | 6/1993 | Vaughn | 128/207.18 |
| 5,284,134 | 2/1994 | Vaughn et al. | 128/DIG. 26 |
| 5,513,634 | 5/1996 | Jackson | 128/207.18 |

Primary Examiner—Edgar S. Burr
Assistant Examiner—Daniel J. Colilla
Attorney, Agent, or Firm—Malin, Haley, DiMaggio & Crosby, PA

[57] ABSTRACT

An oxygen delivery conduit for supplying oxygen continuously under pressure (above atmospheric pressure) to a patient wearing a nasal cannula that prevents occlusion or pinching of the oxygen tube sections supplying the oxygen to insure a continuous oxygen supply to the patient. First and second oxygen supply tube sections rotate relative to each other freely while sealed to prevent crimping, pinching or occlusion of the tubing. The rotatable coupling includes roller or ball bearings mounted in a sealed, non-lubricated bearing structure in a coupling housing.

6 Claims, 3 Drawing Sheets

OCCLUSION RESISTANT OXYGEN SUPPLY CONDUIT FOR A NASAL CANNULA

BACKGROUND OF THE INVENTION

1. Field of the Invention

This invention relates generally to a patient oxygen supply tubing system for supplying oxygen to nasal cannulas and specifically to a patient's oxygen supply system for nasal cannulas that include a pinch or occlusion resistant oxygen tubing to prevent oxygen flow stoppage regardless of patient movement often caused by twisting or severe bending of the oxygen supply tubing.

2. Description of the Prior Art

Nasal cannulas include flexible tubing that can supply pure oxygen directly to the nasal passages of a patient whether in the hospital or in a home environment. Typically an oxygen supply tank (having a pressure relief valve and an outlet metering valve) is connected to an extended patient oxygen supply tube which terminates in dual nasal cannulas for supplying oxygen continuously under pressure from the tank to the patient. The fact that the patient must receive pure oxygen indicates severe health problems. It is imperative that the oxygen supply not be shut off at any time which could result in severe illness or death of the patient. However, because the patient's head is directly connected to the very flexible plastic oxygen supply tube through the nasal cannulas, physical activity and movement by the patient can twist, bend, pinch and distort the oxygen supply tube causing occlusion in the oxygen supply tube because of pinching or occlusive distortion of the tube. Currently, one approach to prevent occlusion in an oxygen supply tube is to "beef up" or strengthen a cross sectional area of the tube with an enlarged cross sectional area design in an attempt to prevent pinching or occlusion.

The present invention provides for a rotatable oxygen supply tubal coupling device that sealably joins tubal ends to permit sections of the oxygen supply tubes to rotate freely relative to each other, preventing pinching or twisting of the oxygen supply tube and therefore occlusion.

While various connectors have been shown in the past that can show universal coupling for health related equipment such that in U.S. Pat. No. 4,484,769, issued Nov. 27, 1984, such devices are not suitable for oxygen supply tubes. U.S. Pat. No. 5,275,444 issued Jan. 4, 1994 shows a swivel hose coupling for pressurized fuel and gas flow systems. U.S. Pat. No. 4,965,846 issued Oct. 23, 1990 shows a pivot pin bearing suited for disposable continuous flow filtration system cartridges that include rotatable elements in the fluid flow. The oxygen supply tubing in accordance with the present invention, since it is attached directly to a patient, must be lightweight, non-complex and is often disposable and must be low cost, at the same time insuring that no possible occlusion or leaking can occur in the tubing.

The present invention overcomes the problems of the prior art by providing an oxygen supply conduit having at least one non-complex rotatably coupling that includes a lubricant free bearing, sized strategically to provide a pressure seal of the supply tube sections which can be conveniently locked together allowing one section of tubing to rotate freely, quickly and easily relative to the adjoining adjacent section of tubing, thereby preventing any type of twist, pinch or occlusion in the tubing regardless of the patient's movement of the supply tube.

SUMMARY OF THE INVENTION

An oxygen supply conduit for nasal cannulas comprising a first flexible oxygen supply tube made of an air tight flexible plastic, a second flexible air tight oxygen supply tube and a rotatable sealable tube coupling, said rotatable coupling having a housing containing a bone dry annular bearing mounted therein.

The first and second oxygen supply tubes are connected together through said coupling housing, permitting free rotation between the first tube and the second tube, preventing twisting of the oxygen supply conduit.

The first end of the first supply tube is connected to a continuous source of pure oxygen required by a patient. The second end of the first supply tube and the first end of the second supply are connected to the rotatable coupling. A second end of the second supply tube is connected to a nasal cannula that supplies oxygen continuously to the patient. The cannula includes some type of device for mounting the nasal cannula securely to the head of the patient.

The oxygen supply conduit can be tube sections of various lengths joined together such that a patient may walk about at home or in a hospital room while still connected to the oxygen supply tank without the supply system being occluded. Each section of oxygen supply conduit is sealably connected and rotatably connected to the adjacent tube sections by at least one rotatable coupling.

Regardless of the relative movement of the supply tube sections caused by the patient, instead of pinching or occluding, the very flexible tubes that supply the oxygen under pressure (normally a few pounds above atmospheric pressure) will rotate about the rotatable coupling rather than twist and fold, which could shut off the oxygen supply.

Using the present invention, one or more rotatable couplings having the bone dry annular ball or barrel or roller bearings provide for bidirectional rotation of individual tube sections, depending on the particular length of the total oxygen supply conduit being used by the patient.

Each oxygen tube section can be constructed of a conventional plastic lumen tubing that is currently being used in hospitals. An example is Baxter product disposable oxygen smooth bore lumen tubing.

Around the inside surface of the connecting end of each oxygen supply tube section, an annular sealing groove is provided that locks the end of each supply tube section to each side of the rotatable coupling. The plastic housing of the rotatable coupling includes an inner cylindrical chamber that receives the outside race of the annular bearing which fits snugly inside and against the cylindrical wall of the cylindrical chamber of the rotatable coupling housing. The rotatable coupling includes an oxygen outlet conduit at one end that has an annular flange that engages and attaches sealably to one end of the oxygen supply tube segment. An intermediate rigid conduit segment is mounted snugly within and passes through inner race of the annular bearing. One end of the intermediate conduit segment has a flared truncated conical end that acts in rotatable contact with the inside of the rotatable coupling housing to prevent or reduce oxygen escape from the supply line. The intermediate conduit also includes; an annular barrier that helps lock the annular bearing in place within the rotatable housing and seal the rotatable housing from oxygen leakage. The intermediate conduit segment also includes a flared tapered flange at its opposite end that allows it to be sealably locked to another end of the oxygen supply tube.

The annular bearing could be a conventional non-lubricated roller bearing or ball bearing that includes an inter race and an outer race, side walls on each side, and is essentially free of any lubricant that might interact with oxygen in a deleterious manner. The side walls are held in place by a lip on the outer race and the inner race and help prevent oxygen leakage.

The inner cylindrical chamber in the rotatable coupling housing includes a recessed portion so that the annular bearing fits sealably and snugly in place and cannot be retracted from the coupling housing. Thus, the annular bearing is locked within the rotatable coupling housing and the intermediate conduit segment with its annular barrier is locked in place with the inner race of the annular bearing. The intermediate conduit segment is also firmly and sealably connected to one end of one oxygen supply tube. One supply tube section connected to the intermediate conduit segment and the inter race of the annular bearing all can rotate relative to the rotatable coupling housing and the outer race of the annular bearing.

One end of the intermediate conduit segment which has a tapered flange at the end physically abuts the outlet passage of the rotatable coupling housing in such a manner that it rotates relative thereto at the same time preventing any significant leakage of oxygen under pressure that is transferred through one oxygen tube relative to the other oxygen supply tube. However, the entire unit renders complete relative motion between the two oxygen supply tubes that are joined together by the rotatable coupling.

To utilize the invention, a complete extended oxygen supply conduit can be formed of any desired length that reaches from the origin of the oxygen supply such as a tank or wall outlet to the cannula attached thereto by using a plurality of oxygen supply tube sections of desired lengths and one or more rotatable couplings sealably connecting the tube sections together. When the oxygen supply is turned on from an oxygen supply tank above atmospheric pressure, the rotatable coupling and the therein will be sealed by a few pounds psi oxygen pressure above atmospheric by the action of the tubing to prevent the escape of oxygen through the rotatable coupling. Thus, a steady supply of oxygen is presented throughout the entire supply system while at the same time the oxygen supply tube cannot be twisted regardless of the movement of the patient which would normally cause occlusion.

The bearing which is used in the present invention is donut shaped and typically includes stainless steel inner and outer races and a plurality of metal or rigid plastic ball bearings or barrel type roller bearings mounted rotatably between the inner and outer annular bearing races and flat plastic side walls to loosely seal the bearings. This swivel system uses stainless steel, plastic bearings with no lubricants to contaminate the oxygen supply type to insure purity of the patient's oxygen supply.

It is an object of this invention to provide improved oxygen supply tubing for a patient nasal cannula that will not pinch or occlude.

It is another object of this invention to permit great mobility by the patient that is connected to an oxygen supply without danger of pinching or shutting off the oxygen supply by providing an oxygen supply conduit that is occlusion resistant.

And yet another object of this invention is to provide oxygen supply conduit that has tubular sections that are rotatable relative to each other and are joined together by a non-complex, inexpensive coupling that is sealable to prevent the escape of oxygen when under pressure.

In accordance with these and other objects which will become apparent hereinafter, the instant invention will now be described with particular reference to the accompanying drawings.

DESCRIPTION OF THE PREFERRED EMBODIMENTS

Figure 1:
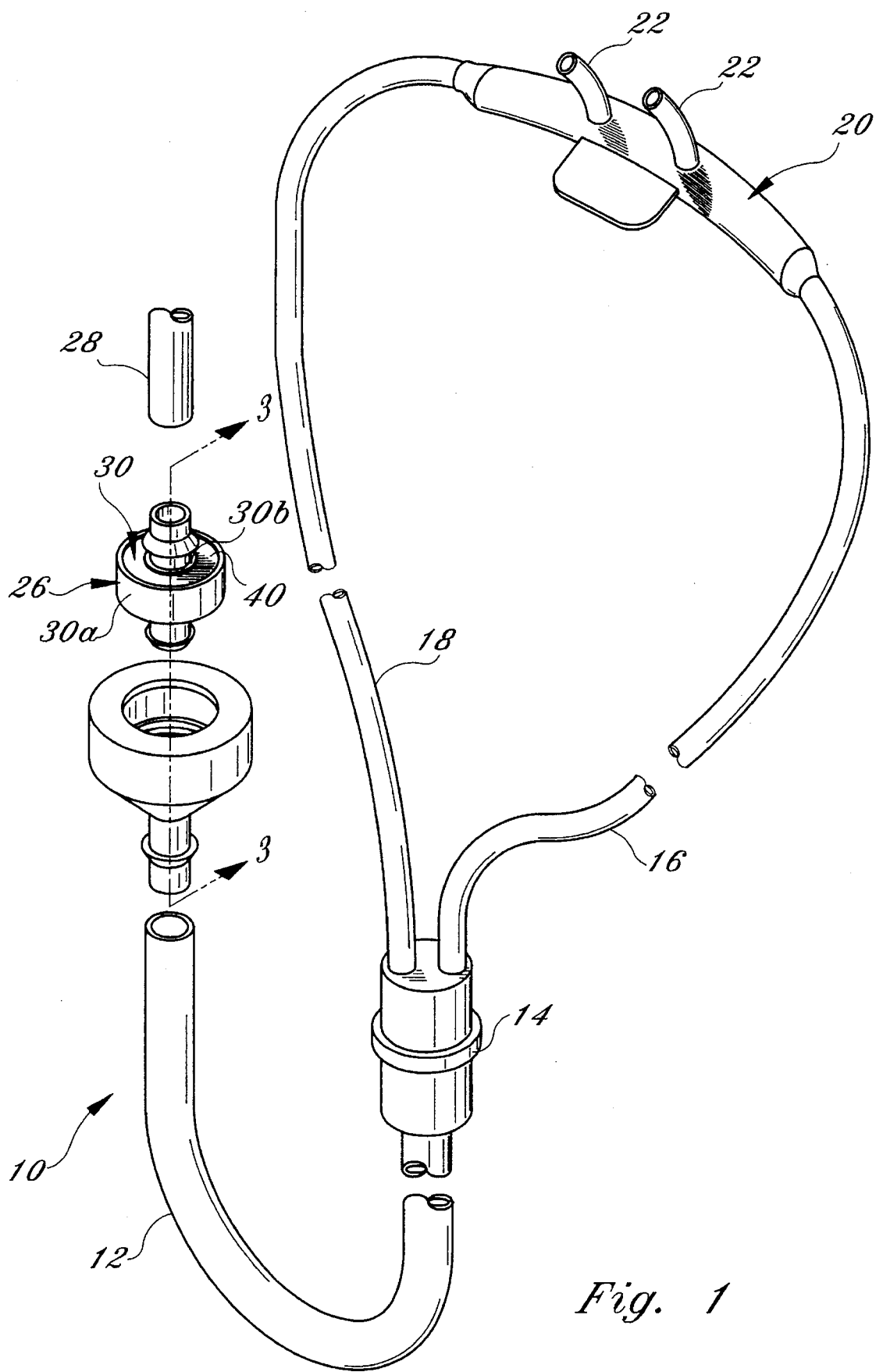
FIG. 1 shows a perspective view of an oxygen supply conduit and a nasal cannula, partially exploded, including a rotatable coupling.

Referring now to the drawings, and in particular FIG. 1, the present invention is shown generally at 10 comprised of a first oxygen supply tube section 12 connected to a joint cannula connector 14 that has two independent oxygen supply tubes 16 and 18, all of which connect into the nasal cannula 20 that has two independent oxygen supply tubes 22 which are typically inserted into the nostrils of the patient.

An oxygen supply tank (not shown) is connected to a rotatable coupling 26 through an oxygen flexible lumen supply tube section 28 shown connected to rotatable coupling 26 through rigid conduit 24.

The purpose of rotatable coupling 26 is to allow rotation between oxygen supply tube section 28 and oxygen supply tube section 12. By virtue of the rotatable coupling, including a rotatable bearing 30 mounted inside rotatable coupling 26 housing 26c, the oxygen flexible supply tube section 28 can be physically rotated in either direction relative to flexible oxygen supply tube section 12. The purpose of this independent rotation, which allows each oxygen tube section to rotate relative to each other, is to prevent any type of twisting, which can be initiated by the movement of the patient walking around with the oxygen supply connected to the cannula attached to the patient.

Flexible tube section 28 contains an annular, specially shaped groove 28a (FIG. 3) near the end of the tube 28 which allows it to be sealably connected to a rigid conduit 24 that is connected to one end of flexible tube section 28 and sealably into the bearing inner race 30b interior passage. The outside of the rotatable coupling 26 is formed of a rigid plastic or metal housing 26c that is unitarily connected to a rigid oxygen conduit 26a and includes an annular flange 26d that allows for a sealable connection between the rotatable coupling 26 and the end of flexible tube section 12.

Figure 3:
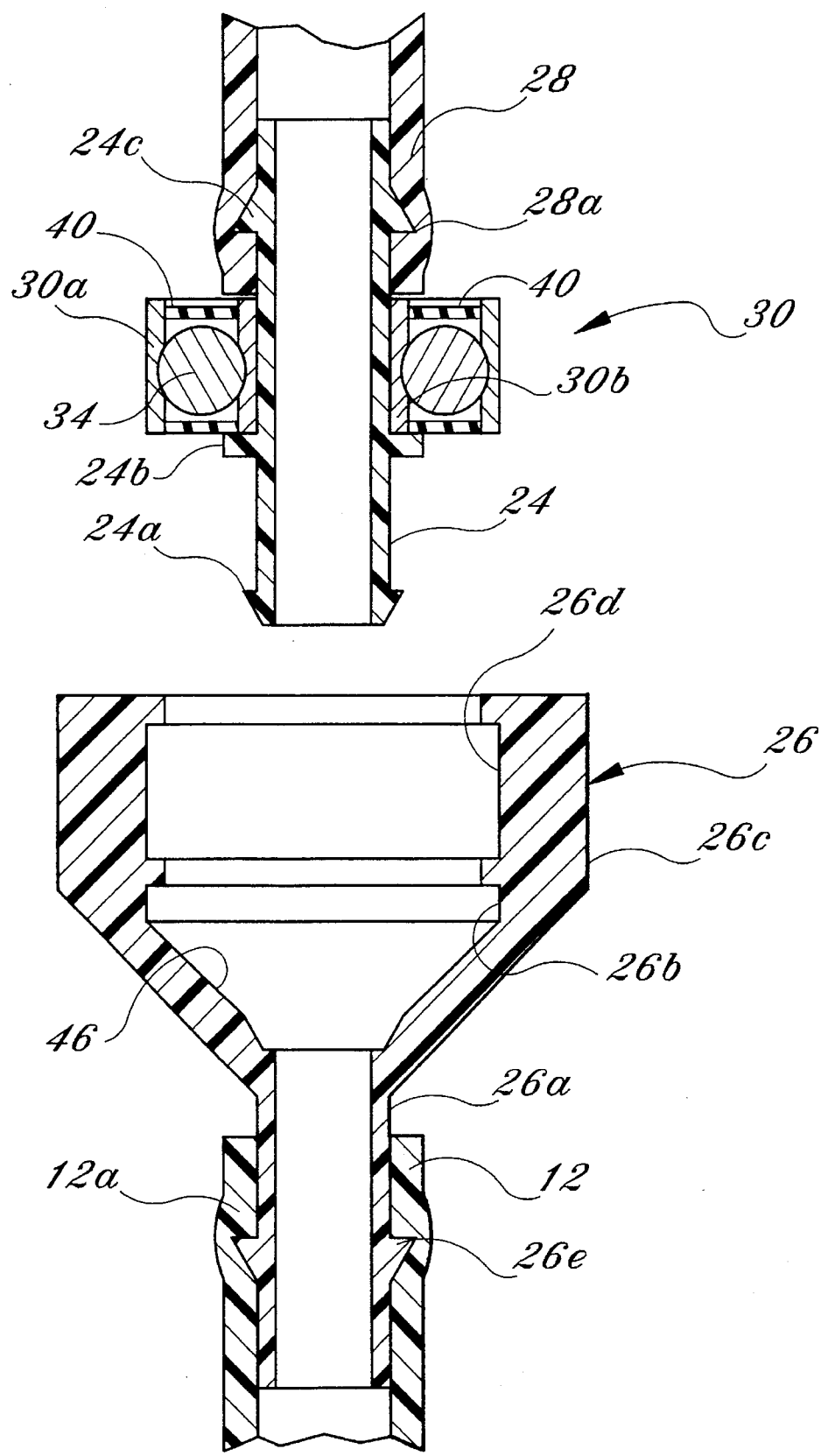
FIG. 3 shows a side elevational view in cross section, exploded, of the rotatable coupling used in the present invention.

Referring to FIG. 3, the rotatable coupling 26 includes a rigid oxygen receiving conduit 26a that is in fluid communication with a cylindrical chamber 26b inside the housing 26c. A rotatable annular bearing 30 includes ball bearings 34, a plurality of which are annularly mounted between an outer race 30a which is a cylindrical or annular ring made of a thin, stainless steel metal having a groove for the ball bearings 34, and an inner stainless steel annular race 30b, all of which makes up the entire bearing. The bearing 30 disclosed shows ball bearings 34 (FIG. 3) (that could be barrel type cylindrical roller bearings) and is made without a lubricant so the entire bearing structure is dry. The outer diameter of the outer race 30a is sized to fit snugly and be held in place inside the recessed portion 26d of cylindrical chamber 26b, whose inside diameter is substantially the same as the outside diameter of outer race 30a so that the bearing, once inserted, will stay firmly in place. The inside diameter of inside race 30b is sized to be approximately the outside diameter of conduit 24 so that conduit 24 fits snugly inside bearing 30.

A rigid plastic conduit 24 allows oxygen to flow therethrough, completing the oxygen supply passage through the rotatable coupling 26 as follows. The cylindrical portion of conduit 24 between an annular flange 24b and the end of tube 28 acts as the support for the inner race of bearing 30 and is mounted therethrough. The bearing 30 is held in place inside of housing 26 as described above. Thus, the bearing 30 holds the conduit 24 in place. A conical portion 46 helps stop oxygen from escaping at the junction of the inside surface of housing chamber 26 and flange 24a. A second, tapered, conical flange 24c near the end of conduit 24 fits snugly in a shaped groove 28a in the flexible tube section 28 that prevents disengagement between the conduit 24 and the flexible oxygen supply tube section 28 and at the same time forming a seal between the end of tube section 28 and the end of conduit 24.

The opposite end of rotatable coupling housing 26 includes a rigid conduit 26A whose outside diameter fits snugly inside of flexible tube section. 12 Tube 12 has a groove 12A near its end to fit snugly and sealably against a conical flange 26E mounted at the end of the housing conduit 26a.

Figure 2:
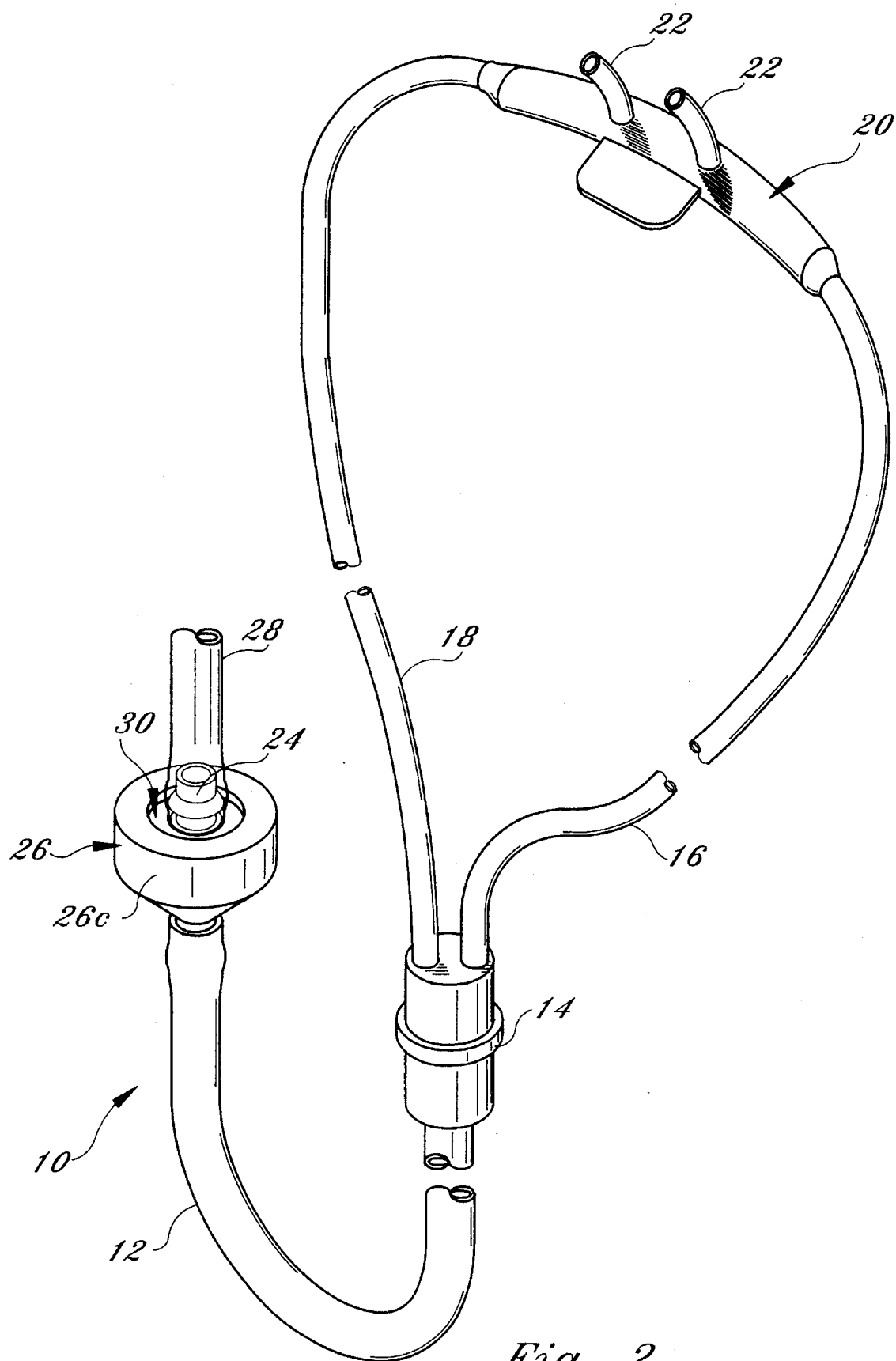
FIG. 2 shows the invention shown in FIG. 1 in perspective.

FIGS. 1 and 2 show the conduit 24 in an exploded view relative to the rotatable coupling 26. Once conduit 24 is firmly and sealably in place inside of bearing 30, the rotatable coupling will not leak oxygen when oxygen under pressure is received through supply tube section 28 from an oxygen source under pressure (2 or 3 pounds psi above atmospheric) as the oxygen flows through the rotatable coupling into conduit 26a and then into supply tube section 12.

The rotatable coupling 26 allows rotation between the outer bearing race 30a and inner bearing race 30b, thus allowing free rotational movement of supply tube section 28 relative to supply tube section 12. By permitting relative rotational movement, twisting the supply tube section 12 or the supply tube section 28 will not pinch or cause stoppage or occlusion of oxygen flowing through the system to the cannula 20. Thus, the patient can freely move about without fear or danger of twisting the flexible tubing in such a way that would cut off the oxygen supply.

In a typical application as shown in FIG. 2, oxygen can be supplied from a tank or wall connection leading to a tank that is connected directly to an oxygen supply tube 28. In this embodiment, only one rotatable coupling 26 is used. For longer embodiments of the invention, additional rotatable couplings 26 can be used along various length tube sections 12 or 28 of the oxygen conduit.

The rotatable coupling 26 includes a dry bearing and material such as stainless steel or even a plastic that will not chemically interact with pure oxygen flowing through the system to insure that the oxygen supplied to the patient is pure.

The ball bearing 30 includes a pair of disc-shaped ball bearing retainers 40 which isolate the ball bearings 34 from outside the bearings and act as supports between the inner and outer races 30a and 30b, forming a unit bearing where the ball bearings are shielded from the outside environment. The retainer 40 fits on each side of the bearings.

The instant invention has been shown and described herein in what is considered to be the most practical and preferred embodiment. It is recognized, however, that departures may be made therefrom within the scope of the invention and that obvious modifications will occur to a person skilled in the art.

What I claim is:

1. An oxygen delivery supply conduit that resists occlusion or pinching for connecting a means for supplying oxygen to a nasal cannula comprising:

a first flexible oxygen supply tube connected at a first end to means for supplying oxygen;

a second flexible oxygen supply tube connected at a first end to a nasal cannula;

a rotatable coupling means having an oxygen inlet conduit connected to a second end of said first oxygen supply tube and an oxygen outlet conduit connected to a second end of said second oxygen supply tube and in fluid communication sealably to the second end of said first oxygen supply tube, said rotatable coupling having a means for permitting rotation of said inlet conduit relative to said outlet conduit said inlet and outlet conduits move rotationally relative to each other preventing occlusion or pinching of said oxygen supply conduit; and said oxygen inlet conduit including a tubular portion ending in a tapered flange and said oxygen outlet conduit including a conical portion sized to rotatably receive said tapered flange;

said rotatable coupling including a rotatable bearing and a housing that includes a cylindrical recessed portion and a tubular end portion in fluid communication, said housing including said cylindrical recessed portion sized to sealably receive an outer diameter of said rotatable bearing;

said oxygen inlet conduit sealably connected within an inner diameter of said rotatable bearing.

2. An oxygen supply conduit as in claim 1 wherein:

said rotatable bearing includes a plurality of non-lubricated ball bearings, an inner race, an outer race, and a pair of ball bearing retainers, said ball bearings being mounted between said inner race and said outer race, said rotatable bearing including a sealable portion; said sealable portion sealing said ball bearings inside between said inner race and said outer race and between said pair of ball bearing retainers, said inner race movable relative to said outer race.

3. An oxygen delivery system as in claim 1, wherein:

said rotatable bearing includes cylindrical roller bearings, an inner race and an outer bearing race, said cylindrical roller bearings being mounted between said inner race and said outer race, said outer race sealably mounted within said cylindrical recessed portion of said housing and said oxygen inlet tube having an outer diameter sized to sealably fit within the inner race of said rotatable bearing thereby preventing the outflow of oxygen.

4. An oxygen supply conduit as in claim 1, wherein said first tube and said second tube are flexible plastic.

5. An oxygen supply conduit as in claim 1, wherein said rotatable coupling means is sealed to prevent the escape of oxygen under pressure.

6. An oxygen supply conduit as in claim 1, wherein said rotatable coupling means is free of lubricants.

* * * * *